US011596307B2

(12) United States Patent
Dastgheib et al.

(10) Patent No.: US 11,596,307 B2
(45) Date of Patent: Mar. 7, 2023

(54) SYSTEMS AND METHODS FOR ACTIVATING A CIRCUIT OF AN IMPLANT DEVICE

(71) Applicant: Verily Life Sciences LLC, South San Francisco, CA (US)

(72) Inventors: Alireza Dastgheib, Mountain View, CA (US); Johan Vanderhaegen, Cupertino, CA (US)

(73) Assignee: VERILY LIFE SCIENCES LLC, South San Francisco, CA (US)

(*) Notice: Subject to any disclaimer, the term of this patent is extended or adjusted under 35 U.S.C. 154(b) by 596 days.

(21) Appl. No.: 16/561,911

(22) Filed: Sep. 5, 2019

(65) Prior Publication Data

US 2019/0387971 A1    Dec. 26, 2019

Related U.S. Application Data

(62) Division of application No. 15/699,471, filed on Sep. 8, 2017, now Pat. No. 10,448,833.

(Continued)

(51) Int. Cl.
*A61B 5/00* (2006.01)
*A61B 5/07* (2006.01)
(Continued)

(52) U.S. Cl.
CPC ............ *A61B 5/0031* (2013.01); *A61B 5/076* (2013.01); *A61B 5/14532* (2013.01);
(Continued)

(58) Field of Classification Search
CPC ........ A61B 5/0031; A61B 5/076; A61B 5/378
See application file for complete search history.

(56) References Cited

U.S. PATENT DOCUMENTS 6,175,752 B1    1/2001  Say et al.
6,809,653 B1 * 10/2004  Mann ................. A61B 5/14532
                                                         604/506
(Continued)

FOREIGN PATENT DOCUMENTS

CN    104323781    2/2015
CN    105102971    11/2015
(Continued)

OTHER PUBLICATIONS

U.S. Appl. No. 15/699,471, "Non-Final Office Action", dated Jan. 18, 2019, 13 pages.
(Continued)

*Primary Examiner* — William J Levicky
(74) *Attorney, Agent, or Firm* — Kilpatrick Townsend & Stockton LLP

(57) ABSTRACT

The present disclosure relates to systems and methods for activating a circuit of an implant device. Consistent with one implementation, an implant device is provided with a sensor including a working electrode (WE) and a counter electrode (CE). The sensor may be configured to generate a first current at the CE when the implant device is implanted in a body of a subject. A sensing circuit may also be provided that is electrically coupled to the WE of the sensor. The sensing circuit may be activated based on the first current and utilize the sensor to measure one or more parameters of an individual or other subject.

18 Claims, 10 Drawing Sheets

Related U.S. Application Data

(60) Provisional application No. 62/397,582, filed on Sep. 21, 2016.

(51) Int. Cl.
*A61N 1/378* (2006.01)
*A61B 5/145* (2006.01)
*A61B 5/1486* (2006.01)
*A61B 5/11* (2006.01)
*A61N 1/372* (2006.01)

(52) U.S. Cl.
CPC ........ *A61B 5/14865* (2013.01); *A61B 5/6861* (2013.01); *A61N 1/378* (2013.01); *A61B 5/11* (2013.01); *A61B 2560/0209* (2013.01); *A61B 2560/0406* (2013.01); *A61B 2560/0468* (2013.01); *A61B 2562/028* (2013.01); *A61N 1/37235* (2013.01)

(56) References Cited

U.S. PATENT DOCUMENTS

| | | | |
|---|---|---|---|
| 2008/0000779 A1 | 1/2008 | Wang et al. | |
| 2008/0278331 A1 | 11/2008 | Hayter et al. | |
| 2008/0281179 A1* | 11/2008 | Fennell | A61B 5/1473 600/347 |
| 2009/0030293 A1* | 1/2009 | Cooper | A61B 5/0031 600/310 |
| 2010/0213057 A1 | 8/2010 | Feldman et al. | |
| 2014/0209481 A1 | 7/2014 | Pletcher et al. | |
| 2016/0242685 A1 | 8/2016 | DeHennis et al. | |

FOREIGN PATENT DOCUMENTS

| | | |
|---|---|---|
| CN | 105581781 | 5/2016 |
| TW | 201614970 | 4/2016 |
| WO | 2016059635 | 4/2016 |

OTHER PUBLICATIONS

U.S. Appl. No. 15/699,471, "Notice of Allowance", dated Jun. 10, 2019, 8 pages.
U.S. Appl. No. 15/699,471, "Restriction Requirement", dated Oct. 11, 2018, 10 pages.
Chinese Application No. 201780058277.1, "Office Action", dated Mar. 6, 2020, 13 pages.
International Application No. PCT/US2017/048664, "International Preliminary Report on Patentability", dated Apr. 4, 2019, 12 pages.
International Application No. PCT/US2017/048664, "International Search Report and Written Opinion", dated Feb. 20, 2018, 18 pages.
International Application No. PCT/US2017/048664, "Invitation to Pay Add'l Fees and Partial Search Report", dated Dec. 18, 2017, 12 pages.
Chinese Application No. 201780058277.1, Notice of Decision to Grant, dated Sep. 10, 2020, 5 pages.
Taiwan Application No. 106131661, Office action dated Apr. 16, 2021 (Machine Translation).

* cited by examiner

SYSTEMS AND METHODS FOR ACTIVATING A CIRCUIT OF AN IMPLANT DEVICE

CROSS-REFERENCE TO RELATED APPLICATIONS

This application is a divisional of U.S. patent application Ser. No. 15/699,471, filed Sep. 8, 2017, which claims priority to U.S. Provisional Patent Application No. 62/397,582, filed Sep. 21, 2016, titled "Systems and Methods for Activating a Circuit of an Implant Device," the entireties of both of which are hereby incorporated by reference.

TECHNICAL FIELD

The present disclosure generally relates to systems and methods for activating a circuit of an implant device. More specifically, and without limitation the present disclosure relates to systems and methods for activating a circuit of an implant device with power from a battery or other source in response to detecting that the device has been implanted in a body of an individual or other subject.

BACKGROUND

A wide variety of implant devices exist today for various applications and uses. For example, an endoscopic capsule may be implanted to perform telemetry within the gastrointestinal tract of a patient. As another example, a brain-computer interface may be implanted to augment and/or repair various cognitive and sensory-motor functions. As a still further example, implanted micro sensors may be utilized for sensing physiological parameters of an individual. These and other implant devices may include various subsystems for collecting data, providing outputs based on collected data, performing calculations, and/or carrying out various instructions.

Implant devices are often small in size and/or include integrated components. Therefore, accessing, replacing, and/or rearranging the internal components of an implant device can be challenging or prohibitive. For example, it may be difficult to replace or rearrange components because some of the internal components are encapsulated with sealant at the time of manufacture. As another example, altering or changing internal components may be difficult because the handling of the components requires complex, expensive equipment and/or techniques that may not be available or known to those other than the manufacturer. As a result, the internal components of implant devices, including the battery, are typically fully assembled and wired at the time of manufacture, and not subject to change or replacement thereafter.

The battery of an implant device can begin draining after manufacture and assembly of the device. In cases where the battery is not readily accessible or changeable, it is necessary to maximize the shelf life of the battery and operational use of the implant device. Therefore, the amount of power consumed by the internal components prior to use of the implant device needs to be minimized.

One method of reducing the amount of power consumed prior to use of the device is to deactivate a portion of the implant device during storage and activate the portion of the implant device shortly before use. For example, an implant device may be configured to detect unpacking of the package containing the implant device and activate the supply of power from the battery only after detecting the unpacking of the package. However, this approach requires additional components to detect the unpacking of the device (such as a magnet and reed relay) and can increase the overall unit cost of the implant device.

Another approach for restricting the amount of power consumption is to deactivate a portion of the implant device during storage and periodically activate the portion of the implant device to detect whether the implant device has been implanted. While this method may eliminate the need for additional components to detect unpacking, power from the battery is still consumed each time the portion of the implant device is activated. Therefore, this approach may require a larger and more expensive battery to provide a sufficient power source for periodically activating the implant device and for subsequent use after unpacking. As a result, it may not be suitable for many applications.

Accordingly, existing systems and methods for activating an implant device do not address the challenge of minimizing the number of components and prolonging shelf life of the device, without increasing the power requirements of the battery or overall expense of the device.

SUMMARY

The present disclosure generally relates to systems and methods for activating a circuit of an implant device. As further described herein, embodiments of the present disclosure include systems and methods that are capable of activating a circuit of an implant device upon implantation of the device in a subject, while minimizing the number of components and power requirements of the device. Embodiments of the present disclosure also include systems and methods that are capable of activating a circuit of an implant device upon electrical coupling of a sensor to the device.

In accordance with one example embodiment, an implantation detector of an implant device is electrically coupled to a counter electrode (CE) of a sensor. The sensor is configured to generate current at the CE when the implant device is implanted in a body of an individual or other subject. The implantation detector may include a clock signal generator that generates a clock signal, and a switch located between the CE of the sensor and ground that shorts the CE with ground based on the clock signal. The implantation detector may also include a voltage detector that detects a voltage at the CE of the sensor and activates a sensing circuit for measuring a physiological parameter of the individual or other subject, the sensing circuit being electrically coupled to a working electrode (WE) of the sensor based on the voltage at the CE of the sensor.

In accordance with another example embodiment, an implant device is provided that includes a sensor with a WE and a CE. The sensor may generate a first current at the CE when the implant device is implanted in a body of an individual or other subject. The implant device may further include a sensing circuit for measuring a physiological parameter of the individual or other subject, the sensing circuit being electrically coupled to the WE of the sensor and an implantation detector that activates the sensing circuit based on the first current.

In accordance with yet another example embodiment, a method for activating a circuit for measuring a physiological parameter of an individual is provided. The method includes providing a sensor including a WE and a CE, the WE of the sensor being electrically coupled to the sensing circuit. The method further comprises generating a first current at the CE of the sensor in response to implantation of the implant device in a body of the individual and activating the sensing circuit based on the first current in response to the generation of the first current.

In accordance with an example embodiment, an implant device is provided that includes a sensor interface configured to interface with a sensor, and a sensing circuit that measures at least one physiological parameter of an individual. The implant device may further include a sensor detector configured to detect whether the sensor is interfacing with the sensor interface and activate the sensing circuit based on the detection.

In accordance with another example embodiments, a method is provided for activating a sensing circuit of an implant device for measuring at least one physiological parameter of an individual. The method includes providing a sensor interface that is configured to interface with a sensor, detecting whether the sensor is interfacing with the sensor interface, and activating the sensing circuit based on the detection of whether the sensor interfacing with the sensor interface.

Before explaining example embodiments of the present disclosure in detail, it is to be understood that the disclosure is not limited in its application to the details of construction and to the arrangements of the components set forth in the following description or illustrated in the drawings. The disclosure is capable of embodiments in addition to those described and of being practiced and carried out in various ways. Also, it is to be understood that the phraseology and terminology employed herein, as well as in the abstract, are for the purpose of description and should not be regarded as limiting.

As such, those skilled in the art will appreciate that the conception and features upon which this disclosure is based may readily be utilized as a basis for designing other structures, methods, and systems for carrying out the several purposes of the present disclosure. Furthermore, the claims should be regarded as including such equivalent constructions insofar as they do not depart from the spirit and scope of the present disclosure.

BRIEF DESCRIPTION OF DRAWINGS

The accompanying drawings, which are incorporated in and constitute part of this specification, and together with the description, illustrate and serve to explain the principles of various exemplary embodiments.

DETAILED DESCRIPTION OF EXAMPLE EMBODIMENTS

Embodiments of the present disclosure provide improved systems and methods for activating a portion of an implant device with power from a battery by detecting that the implant device is implanted in the body of a subject. The disclosed embodiments are capable of detecting that an implant device is implanted in the body of a subject, while minimizing the number of required components and the amount of power used for detecting the implantation.

Reference will now be made in detail to the embodiments implemented according to the disclosure, the examples of which are illustrated in the accompanying drawings. Wherever possible, the same reference numbers will be used throughout the drawings to refer to the same or like parts.

Figure 1:
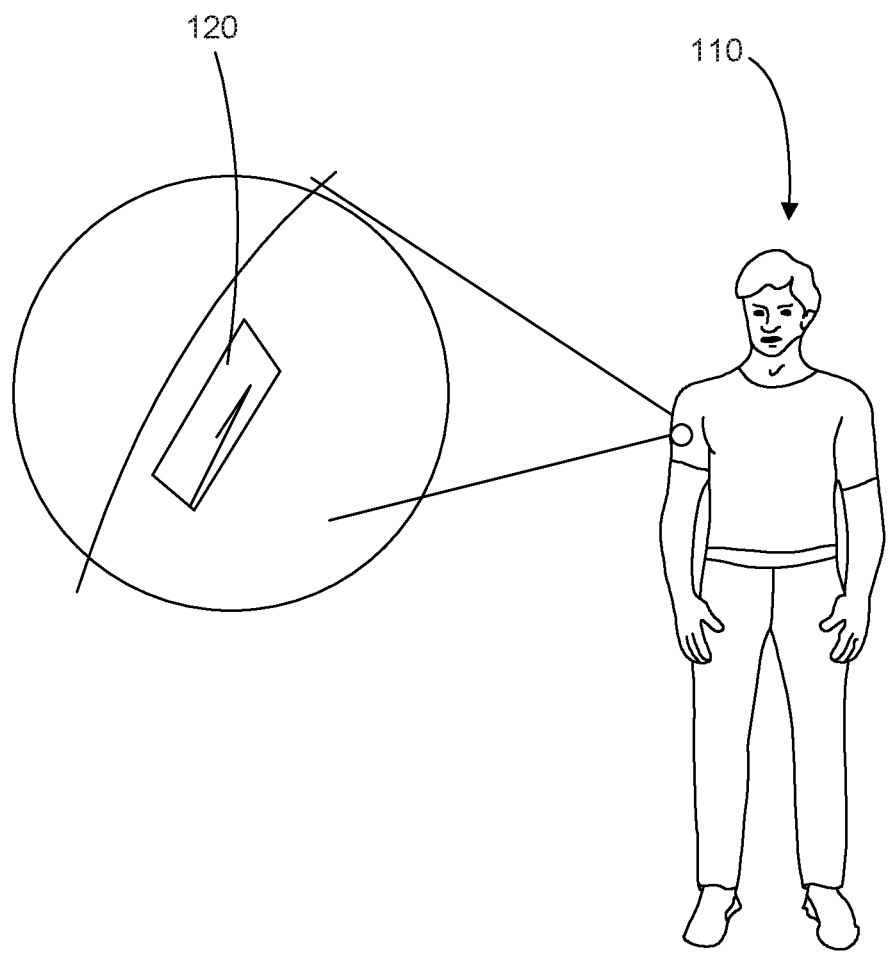
FIG. 1 depicts an example system environment for implementing embodiments of the present disclosure.

FIG. 1 depicts an example system environment 100 for implementing embodiments of the present disclosure. As shown in FIG. 1, system environment 100 includes an implant device 120. In some embodiments, implant device 120 is positioned in a subject 110. Subject 110 may be a human subject as shown in FIG. 1. Alternatively, subject 110 may be an animal subject or any other type of living subject. The size and dimensions of implant device 120 may be vary depending on the needs or particular use(s) of the device. In some embodiments, implant device 120 may be a centimeter implanted device (i.e., a device having size dimensions at least one centimeter each), a millimeter implanted device (i.e., a device having size dimensions less than one centimeter but at least one millimeter each), or a sub-millimeter implanted device (i.e., a device having size dimensions less than one millimeter each).

Implant device 120 may be capable of being implanted at various locations and at various depths within the body of subject 110. While implant device 120 is shown in FIG. 1 as being implanted in the arm of subject 110, other implant locations are contemplated and the illustrated example is in no way intended to be limiting on the embodiments of the present disclosure.

Implanted device 120 may measure various parameters of subject 110. In some embodiments, implant device 120 may include a system for continuously measuring the glucose level of subject 110. In some embodiments, implant device 120 may further include one or more subsystems for sensing the glucose level and/or other parameter(s) of subject 110, providing the measured data to an external monitoring system, and/or storing the measured data. In some embodiments, implant device 120 may further include a subsystem for interacting with another implanted device. For example, implant device 120 may include a subsystem for providing the measured glucose level to another device (implanted and/or external) that delivers insulin to subject 110. Other example subsystems may be used in conjunction with the disclosed embodiments, however, and the enumerated examples are in no way intended to be limiting on the scope of the present disclosure.

Figure 2:
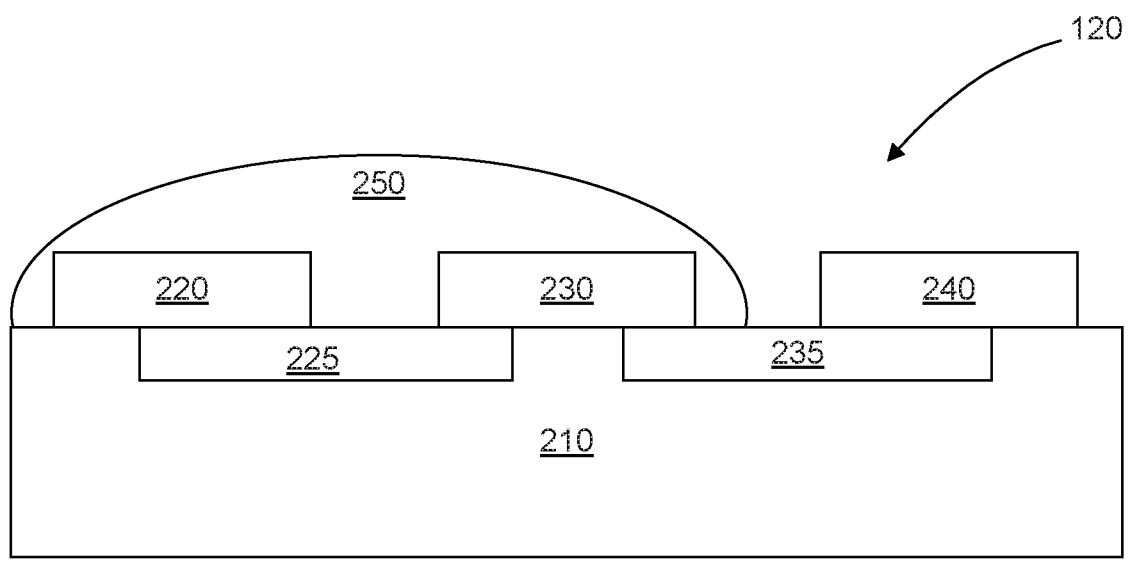
FIG. 2 is a cross-sectional view of an implant device implementing embodiments consistent with the present disclosure.

FIG. 2 is a cross-sectional view of an exemplary implant device 120. As shown in FIG. 2, implant device 120 includes a number of components. It will be appreciated from the present disclosure that the number and arrangement of these components is exemplary only and provided for purposes of illustration. Other arrangements and numbers of components may be utilized without departing from the teachings and embodiments of the present disclosure.

As shown in FIG. 2, implant device 120 includes a battery 220, a microchip 230, and a sensor 240, which are mounted on a substrate or circuit board 210. In some embodiments, one or more of battery 220, microchip 230, and sensor 240 may be inside or partially inside circuit board 210. Further, in some embodiments, circuit board 210 may include interconnect 225 and interconnect 235 that electrically interconnect battery 220 to microchip 230 and microchip 230 to sensor 240, respectively. Interconnects 225 and 235 may be implemented using copper or another suitable metal layer for interconnecting the components of implant device 120.

In some embodiments, sensor 240 may be implemented as an electrochemical sensor. Electrochemical sensors operate by reacting with the stimuli of interest (i.e., "analyte") and producing an electrical signal proportional to the concentration of the analyte. The analyte may react at the surfaces of a working electrode (WE) and/or a counter electrode (CE) involving either an oxidation and/or reduction mechanism. These reactions may be catalyzed by the electrode materials specifically developed for the analyte.

In some embodiments, when sensor 240 becomes in contact with the analyte for the first time (e.g., when the sensor is first implanted in the body of subject 110), a large, amperometric current may be initially drawn or generated at the WE and CE of the sensor, for example, due to instantaneous reduction of oxygen at the surface of the CE and/or oxidation at the surface of the WE. As the electrochemical reactions continue, however, the amperometric current decreases to a steady-state range that is approximately proportional to the analyte concentration at the electrodes.

Microchip 230 may be, for example, an application-specific integrated circuit (ASIC) or any other component(s) containing electronic circuits (e.g., discrete circuit elements and field-programmable gate array (FPGA)). In some embodiments, implant device 120 may further include sealant 250 encapsulating battery 220 and/or microchip 230 so as to prevent the components from becoming in direct contact with the body of subject 110. In some embodiments, sealant 250 may be a hermetic sealant. In some embodiments, microchip 230 may include a plurality of chips.

A portion of microchip 230 may be deactivated before implant device 120 is implanted in the body of subject 110 to maximize the shelf life of implant device 120. In one example, the portion comprises one or more circuit components of microchip 230 that are deactivated by preventing power from being supplied to them while microchip 230 is stored or not used. The deactivated portion of microchip 230 may be activated after detecting that implant device 120 has been implanted in the body of subject 110. In some embodiments, microchip 230 may be configured to detect the implantation of implant device 120 in the body of subject 110 by, for example, including a circuit to detect the large, initial, amperometric current generated at the CE of electrochemical sensor 240 immediately after sensor 240 first comes into contact with the body of subject 110.

Figure 3:
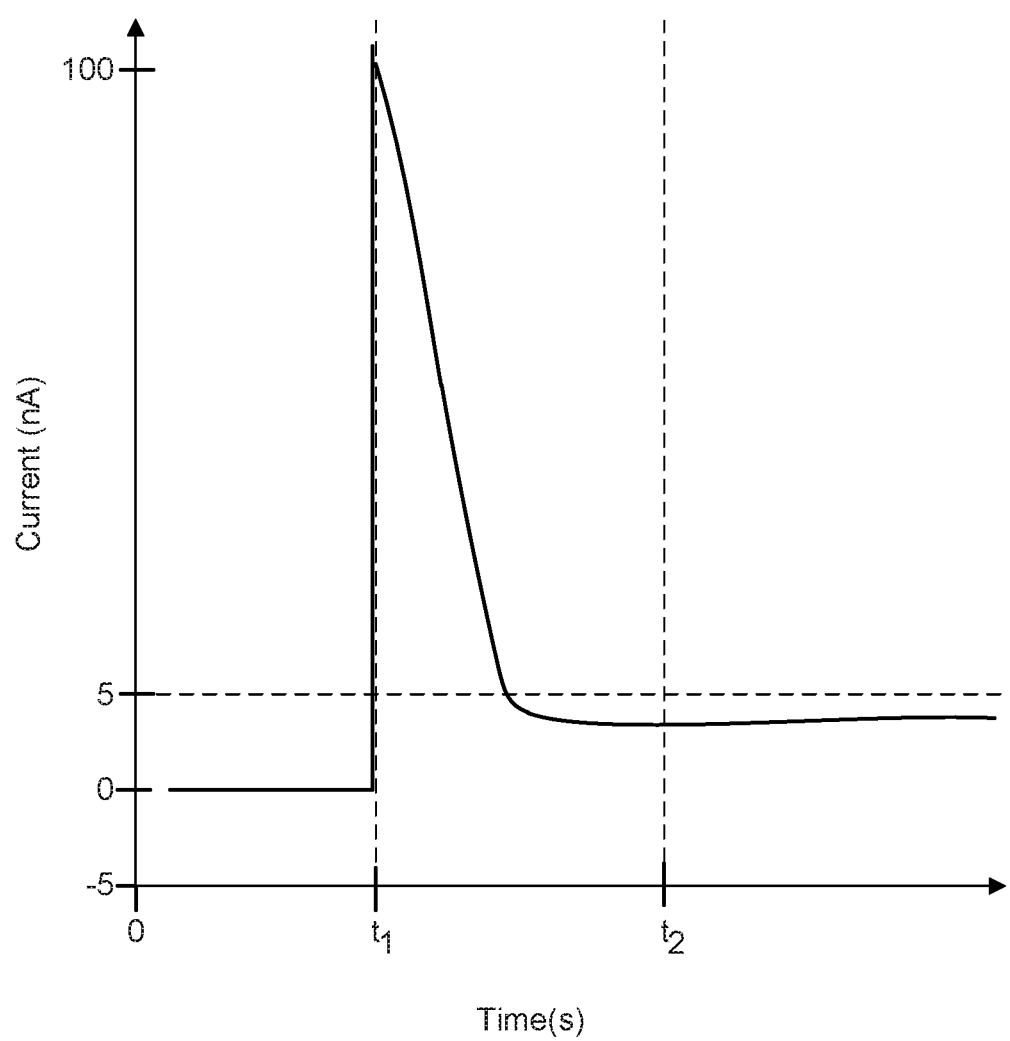
FIG. 3 is a graph showing a transient response of an example electrochemical sensor consistent with embodiments of the present disclosure.

FIG. 3 is a graph 300 showing a transient response of example electrochemical sensor 240 of FIG. 2, consistent with embodiments of the present disclosure. The dependent variable (y-axis) of graph 300 is the amount of current drawn/generated by sensor 240, for example, in nano-amps, and the independent variable (x-axis) of graph 300 is time, for example, in seconds.

At time $t_1$, implant device 120 including sensor 240 is implanted in the body of subject 110. Thus, the time period before $t_1$ represents a period before implant device 120 is implanted in the body of subject 110. Before $t_1$, sensor 240 may generate no current or a negligible amount of current. Immediately after $t_1$ (i.e., immediately after implantation), however, sensor 240 may generate a large, initial, amperometric current. In the example of FIG. 3, electrochemical sensor 240 generates over 100 nA immediately after implant device 120 is implanted in the body of subject 110.

At time $t_2$, which is at a predetermined amount time after $t_1$, the current generated by sensor 240 may decrease to a steady-state range. In the example of FIG. 3, $t_2$ may be 200 seconds after $t_1$, and the steady-state current range may be between 1 nA and 5 nA, for example. After $t_2$, the current drawn/generated by sensor 240 may be proportional to the analyte concentration (e.g., glucose concentration). A skilled artesian may experimentally determine time $t_2$ for a given sensor, for example, based on a graph similar to graph 300.

Figure 4:
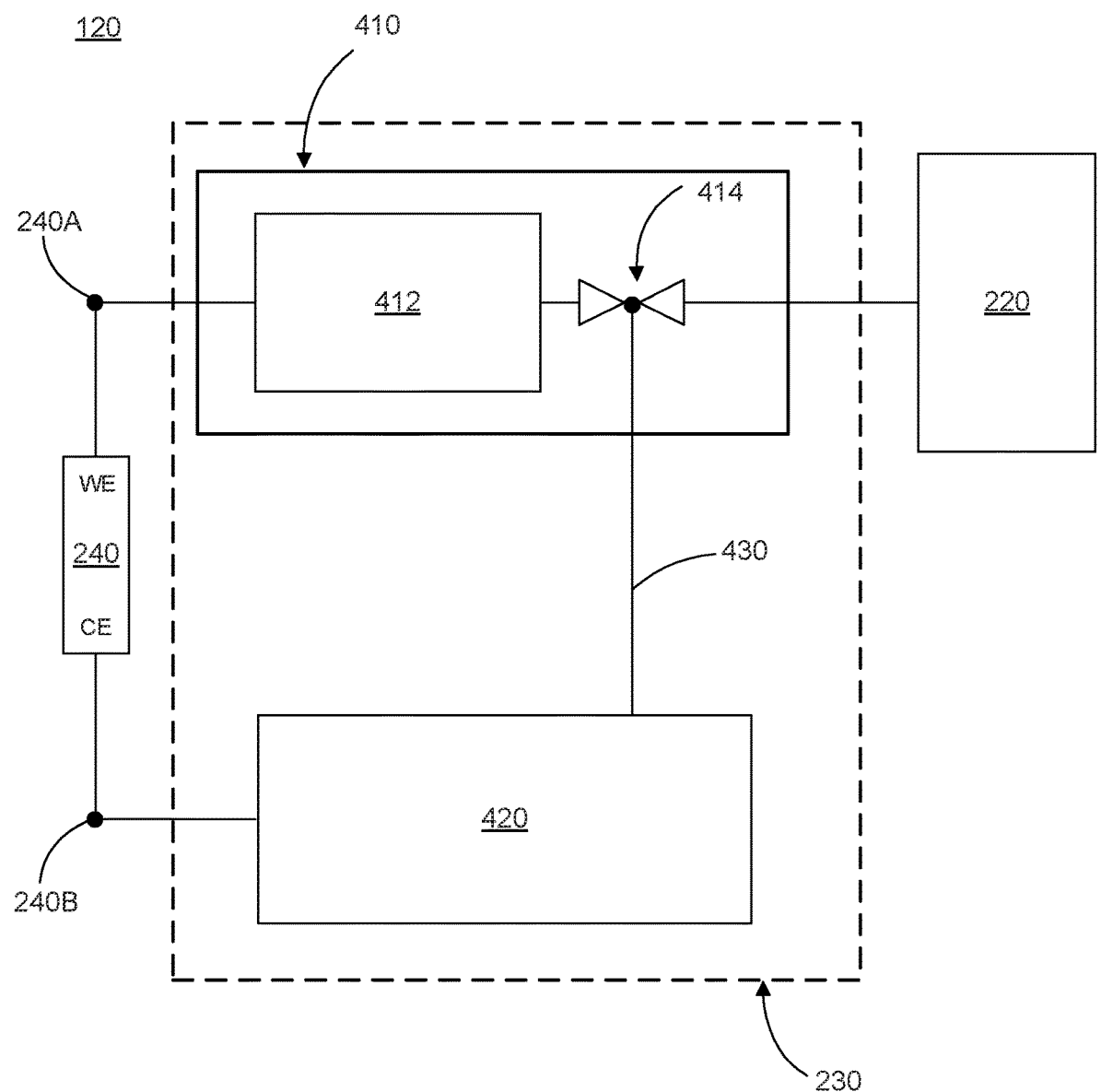
FIG. 4 is a block diagram illustrating an example implant device consistent with embodiments of the present disclosure.

FIG. 4 is a block diagram illustrating a portion of example implant device 120 shown in FIG. 2, consistent with embodiments of the present disclosure. In FIG. 4, electrochemical sensor 240 of implant device 120 includes a working electrode (WE) connected to a WE node 240A and a counter-electrode (CE) connected to a CE node 240B. In some embodiments, electrochemical sensor 240 may further include a reference electrode (RE).

In FIG. 4, microchip 230 may include a sensing circuit 410 for measuring one or more physiological parameter of an individual and an implantation detector circuit 420 for detecting implantation of the implant device in a body of the individual. In the example implant device 120 of FIG. 4, sensing circuit 410 and implantation detection circuit 420 both use a single or common sensor (e.g., electrochemical sensor 240) for measuring one or more physiological parameters of the individual and for detecting implantation of the implant device in the body of the individual.

In alternative embodiments, implant device 120 may include a first sensor for detecting implantation of implant device 120 in a body of an individual and a second sensor for measuring one or more physiological parameter of the individual. In these embodiments, sensing circuit 410 may measure one or more physiological parameters of the individual using the first sensor and implantation detection circuit 420 may use the second sensor to detect implantation of the implant device in a body of the individual. In these embodiments, the first and second sensors may be different type of sensors. For example, the second sensor may be an electrochemical sensor configured to detect one type of physiological parameter(s), while the first sensor is another electrochemical sensor configured to detect another type of physiological parameter(s).

In some embodiments, sensing circuit 410 may measure one or more physiological parameters of the individual using both the first and second sensors. For example, the first and second sensors may be configured to measure the same physiological parameters, and sensing circuit 410 may obtain a more accurate measurement by using both sensors compared to an embodiment using a single circuit. In another example, the first and second sensors may be configured to measure different physiological parameters, and sensing circuit 410 may measure a plurality of physiological parameters using the first and second sensors.

In some embodiments, sensing circuit 410 may be electrically connected to implantation detector circuit 420, for example, via an interconnect 430. Sensing circuit 410 and/or implantation detector circuit 420 may be electrically connected to and powered by battery 220. In some embodiments, microchip 230 may include a first chip including sensing circuit 410 and a second chip including implantation detector circuit 420.

In some embodiments, sensing circuit 410 may operate in one of at least two modes. In a first mode, sensing circuit 410 may be configured to consume zero or substantially zero power from a power source such as battery 220. In FIG. 4, for example, sensing circuit 410 includes one or more switches 414 between one or more portions 412 of sensing circuit 410 and battery 220. Switches 414 may be configured to create an open connection (i.e., preventing current from flowing) between portions 412 and battery 220 while sensing circuit 410 is in the first mode.

In some embodiments, portions 412 of sensing circuit 410 may include an analog-to-digital converter (ADC) arranged to convert the amount of current generated at WE node 240A to a digital signal. Additionally, or alternatively, portions 412 of sensing circuit 410 may include an amplifier (e.g., transimpedence amplifier) for generating a voltage-based signal, or a current-based signal having a larger amplitude compared to the raw signal generated by sensor 240. Furthermore, portions 412 of sensing circuit 410 may include a circuit that generates a voltage-based or current-based signal having a different output impedance. Portions 412 of sensing circuit 410 may further include other circuit(s) for accurately measuring the current generated at WE node 240A.

In a second mode, sensing circuit 410 may be configured to consume sufficient power necessary to sense the current drawn at WE of sensor 240 (i.e. at WE node 240A). For example, in exemplary implant device 120 of FIG. 4, switches 414 may create a closed connection (i.e., allowing current to flow) between portion 412 and battery 220 while sensing circuit 410 is in the second mode. Therefore, the amount of power consumed by sensing circuit 410 in the second mode may be greater than the amount of power consumed by sensing circuit in the first mode.

In some embodiments, the operating mode of sensing circuit 410 may be determined based on an electrical signal from implantation detector circuit 420. For example, a first signal from implantation detector circuit 420 via interconnect 430 may cause sensing circuit 410 to operate in the first mode while a second signal from implantation detection circuit 420 via interconnect 430 may cause sensing circuit 410 to operate in the second mode. In this example, interconnect 430 may be coupled to switches 414 to control the supply of power from battery 220 to portions 412 of sensing circuit 410.

In some embodiments, sensing circuit 410 may switch between one mode to another mode no more than a predetermined number of times. For example, sensing circuit 410 may switch from the first mode to the second mode no more than once, based on an electrical signal from implantation detection circuit 420. In this example, after switching to the second mode, sensing circuit 410 may remain in the second mode irrespective of the electrical signal received from implantation detection circuit 420.

It will be appreciated that a circuit element may be a linear or a non-linear element, such as, but not limited to, a resistor, a capacitor, an inductor, a transistor, a memristor, a diode, a transistor, a switch, a current/voltage source, to provide some examples.

In FIG. 4, WE node 240A is shown to be connected to sensing circuit 310 only; however, it will be appreciated that WE node 240A may be connected to additional circuits including, for example, a circuit providing a bias voltage between WE node 240A and ground. In one example, the bias voltage between the WE and the CE may be 0.5 V.

Further as noted above, the CE of electrochemical sensor 240 may generate a large, initial, amperometric current immediately after electrochemical sensor 240 first comes into contact with the body of subject 110. Implantation detection circuit 420 may detect such amperometric current. For example, implantation detection circuit 420 may include one or more circuit elements arranged to generate a first signal (e.g., at interconnect 430) when zero current or substantially zero current is detected at the CE node 240B and generate a second signal (e.g., at interconnect 430) when current above/below a predetermined, threshold current is detected at the CE node 240B. The threshold current may be set based on the expected initial, amperometric current generated by the electrochemical sensor being used. For example, it will be appreciated by a skilled artisan that the threshold current may be determined by experimentally obtaining a graph of a transient response for the electrochemical sensor being used, similar to graph 300 of FIG. 3.

Figure 5:
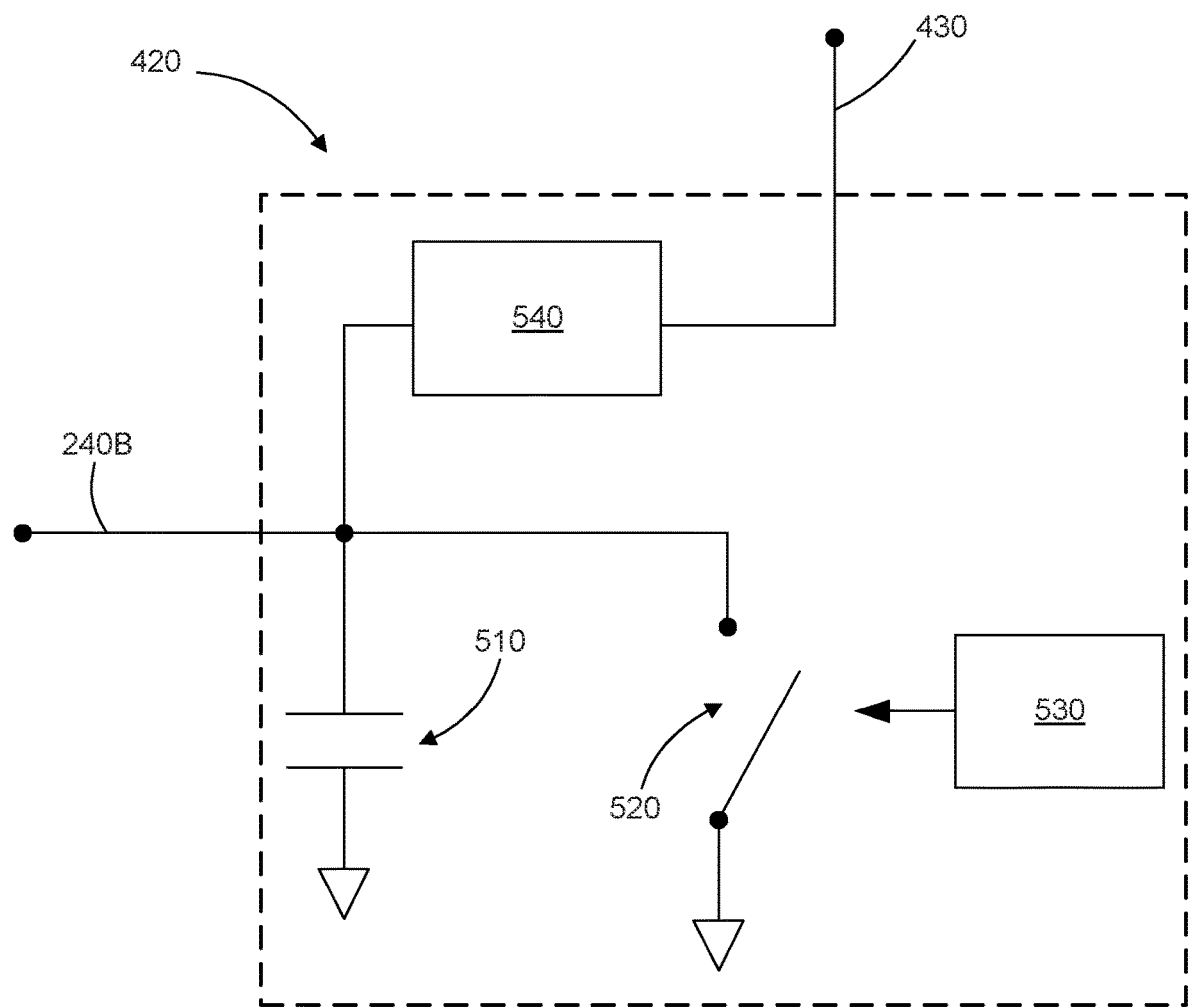
FIG. 5 is a circuit diagram of an example implantation detection circuit consistent with embodiments of the present disclosure.

FIG. 5 is a circuit diagram of an example implantation detection circuit 420 shown in FIG. 4, consistent with embodiments of the present disclosure. As disclosed herein, implantation detection circuit 420 may generate a first signal before implant device 120 is implanted and a second signal after implant device 120 is implanted. The generated signal, as noted above, may be used by sensing circuit 410 to determine the mode of operation. For example, the first signal generated by implantation detection circuit 420 may cause sensing circuit 410 to operate in a first mode while a second signal generated by implantation detection circuit 420 may cause sensing circuit 410 to operate in a second mode.

Example implantation detection circuit 420 of FIG. 5 includes a capacitor 510 between CE node 240B and ground. Capacitor 510 is also arranged to store charges generated at CE node 240B. Implantation detection circuit 420 further includes a switch 520 (e.g., a relay) between CE node 240B and ground. In some embodiments, switch 520 may periodically short CE node 240B to ground. For example, switch 520 may be configured to close or open in response to a signal generated by a clock circuit 530. The periodic shorting of CE node 240B to ground may periodically drain the charges stored by capacitor 510. Therefore, the average amount of current generated at CE node 240B may determine the maximum amount of charge stored in capacitor 150 as well as the maximum voltage between CE node 240B and ground during a single clock cycle.

Example implantation detection circuit 420 of FIG. 5 further includes a threshold detector 540 that generates an output signal based on the detected voltage between CE node 240B and ground. For example, threshold detector 540 may output a first signal when the voltage between CE node 240B and ground is below a threshold voltage and output a second signal once the voltage between CE node 240B and ground is above (or equal to) the threshold voltage. In some embodiments, threshold detector 540 may continue to generate the second signal even when the voltage between CE node 240B and ground subsequently falls below the threshold voltage.

In some embodiments, once threshold detector 540 detects a voltage that is above the threshold voltage, threshold detector 540 may cause switch 520 to close permanently thereby permanently shorting the CE node 240B with ground.

In some embodiments, the first signal and the second signal may be represented by one or more voltage or current levels. For example, the first signal may be represented by the supply voltage of microchip 230, while the second single may be represented by the ground-level voltage.

In some embodiments, the capacitance of capacitor 510 may be between 10 nF and 500 nF, the frequency of the signal generated by clock circuit 530 may be between 10 Hz and 100 Hz, and/or the threshold voltage of voltage threshold detector 440 may be between 50 m V and 1 V.

Figure 6:
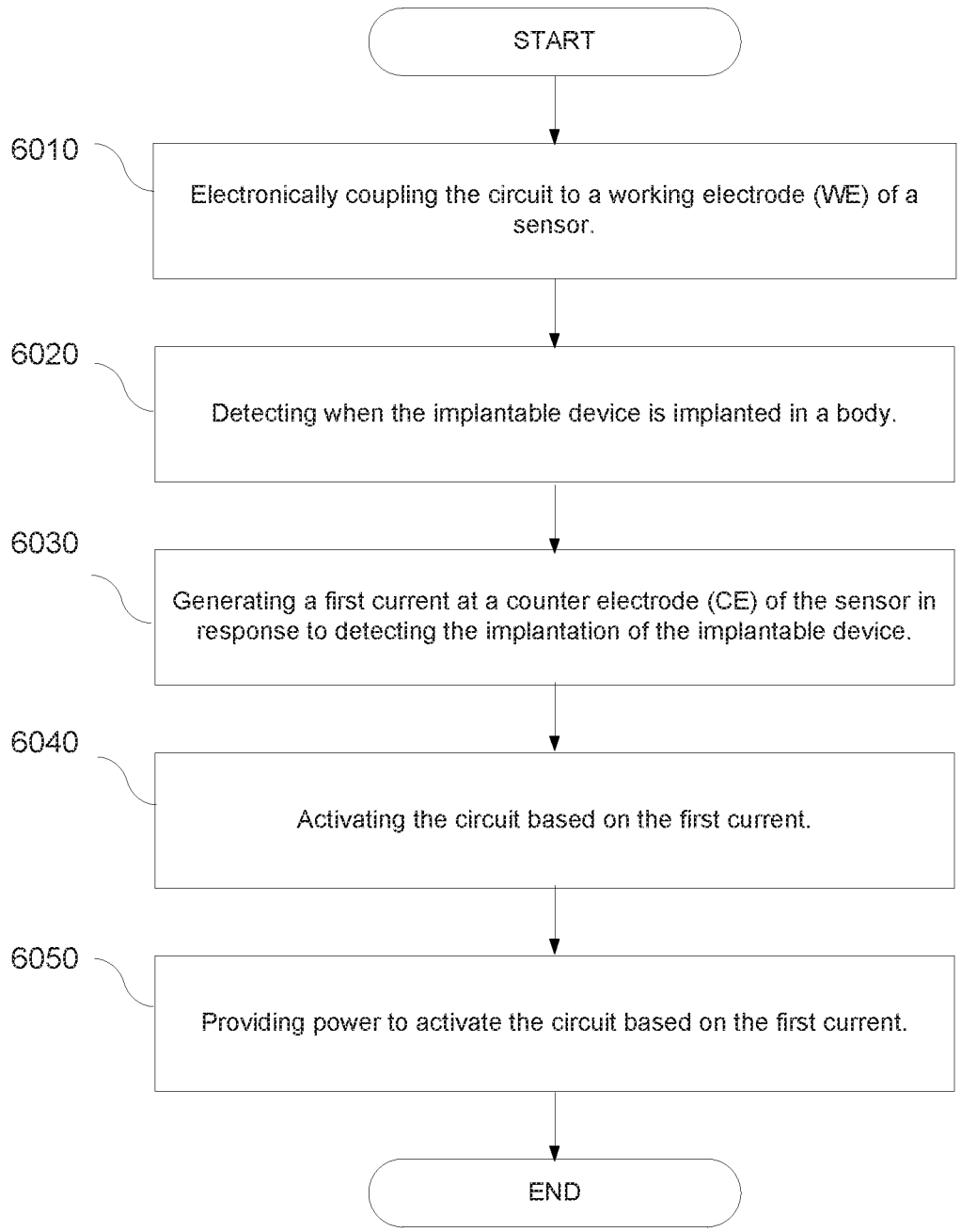
FIG. 6 is a flowchart of an example method consistent with embodiments of the present disclosure.

FIG. 6 is an illustrative process 6000 for activating a circuit for measuring one or more physiological parameters of an individual. At step 6010, a sensor including a WE and a CE is provided. In some embodiments, the WE of the sensor may be electrically coupled to a sensing circuit. At step 6020, a first current is generated at the CE of the sensor in response to implantation of the implant device in a body of the individual. At step 6030, the sensing circuit is activated in response to the generation of the first current. In some embodiments, the activation of the sensing circuit in response to the first current may include generating a clock signal, shorting the CE with ground based on the clock signal, detecting a voltage between the CE of the sensor and ground, and activating the sensing circuit based on the voltage between the CE of the sensor and ground. In some embodiments, the activation of the sensing circuit may further include providing power from a power source to activate the sensing circuit. In some embodiments, the power source may be a battery. At step 6040, the activated sensing circuit may measure one or more physiological parameters of the individual.

Figure 7:
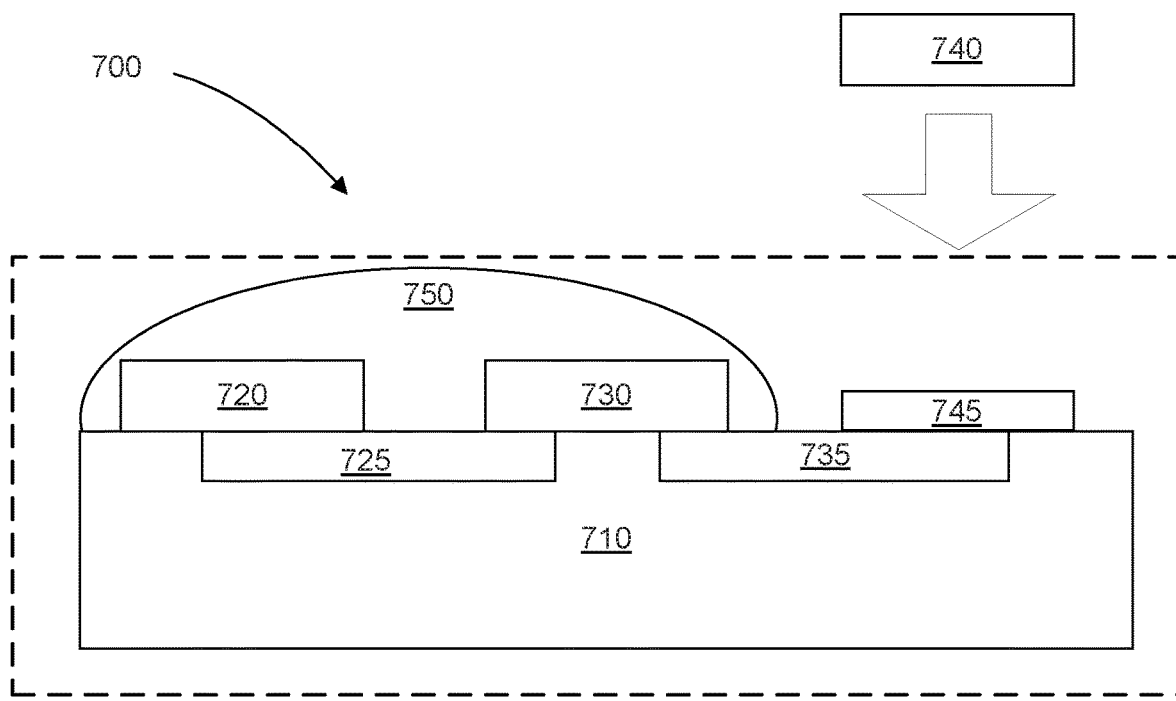
FIG. 7 is a cross-sectional view of an implant device implementing embodiments consistent with the present disclosure.

FIG. 7 is a cross-sectional view of another exemplary implant device 700. As shown in FIG. 7, implant device 700 includes a battery 720 and a microchip 730, which are mounted on a substrate or circuit board 710. Circuit board 710 may include interconnect 725 that electrically interconnects battery 720 to microchip 730. Circuit board 710 may also include interconnect 735 that is electrically connected to microchip 730.

Microchip 730 may be, for example, an ASIC or any other component(s) containing electronic circuits (e.g., discrete circuit elements and FPGA). In some embodiments, implant device 700 may further include sealant 750 encapsulating battery 720 and/or microchip 730 so as to prevent the components from becoming in direct contact with the body of subject 110. In some embodiments, sealant 750 may be a hermetic sealant. In some embodiments, microchip 730 may include a plurality of chips.

FIG. 7 also shows a sensor 740. However, unlike sensor 240 of implant device 120 of FIG. 2, which may be assembled to substrate 210 during the manufacturing process, sensor 740 may be separate from implant device 700 even after the manufacturing process. In some embodiments, sensor 740 and implant device 700 may be configured such that sensor 740 may be assembled to circuit board 710 after the manufacturing process (e.g., by the patient or physician). For example, as shown in FIG. 7, implant device 700 may include a sensor interface 745 that electrically couples sensor 740 with microchip 730 (via interconnect 735). Further, sensor interface 745 may be configured to facilitate electrical coupling of microchip 730 with sensor 740 after the manufacturing process. For example, sensor interface 745 may be an array of exposed I/O pads that can align and bond to an array of solder balls I/Os of sensor 740.

In some embodiments, sensor interface 745 may be configured such that sensor 740 can be electrically coupled to microchip 730 without tools such as soldering tools, alignment tools, and/or reflow heaters. For example, sensor interface 745 may be a socket-based or slot-based interface that is compatible with electrical interfaces of sensor 740. These interfaces may be used to electrically couple sensor 740 with microchip 730 at the user end (e.g., by the patient, physician, or salesperson).

In some embodiments, sensor interface 745 may be a re-matable interface where sensor 740 can repeatedly de-interface or re-interface with sensor interface 745. Additionally, or alternatively, sensor interface 745 may facilitate repeated electrical coupling and decoupling of sensor 740 with microchip 730. In some embodiments, sensor interface 745 may include a mechanism to hold sensor 740 to circuit board 710. For example, sensor interface 745 may include a mechanical clamp to hold sensor 740 to circuit board 710.

Sensor interface 745 may include an electrical interface to facilitate electrical coupling of sensor 740 with microchip 730 via interconnect 735. In some embodiments, the electrical interface may be a capacitive, resistive, and/or inductive interface.

Sensor 740 may be an electrochemical sensor, an inertial sensor, pressure sensor, light sensor, microphone, or any other sensor that can be implanted to subject 110.

A portion of microchip 730 may be deactivated while sensor 740 is separate from implant device 700 (i.e., while sensor 740 is electrically decoupled from microchip 730 and/or de-interfaced from sensor interface 745) to maximize the shelf life of implant device 700. In one example, the portion comprises one or more circuit components of microchip 730 that are deactivated by preventing power from being supplied to them while sensor 740 is separate from implant device 700. The deactivated portion of microchip 730 may be activated after detecting that sensor 740 has interfaced with sensor interface 745 and/or electrically coupled to microchip 730.

Figure 8:
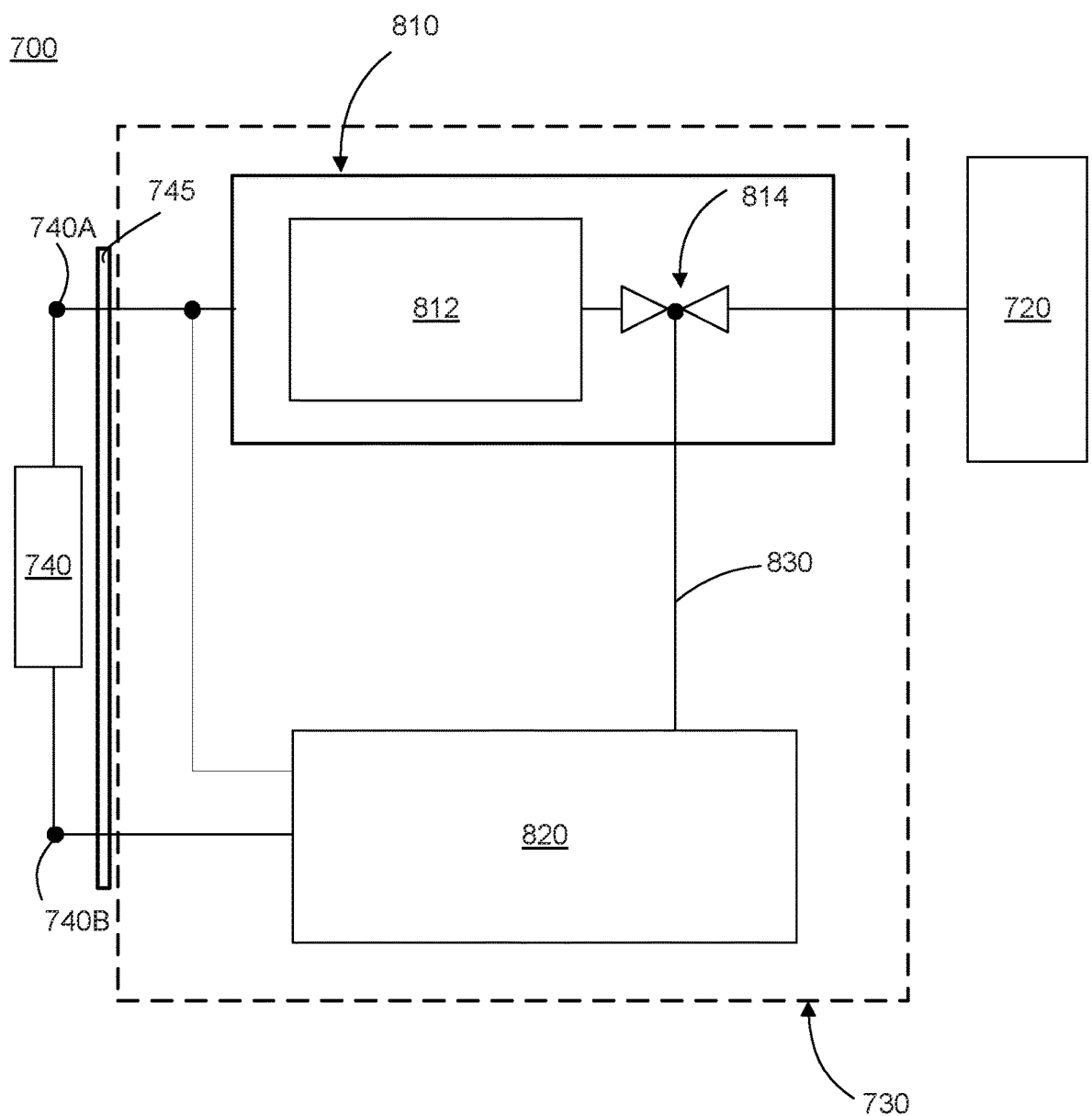
FIG. 8 is a block diagram illustrating an example implant device consistent with embodiments of the present disclosure.

FIG. 8 is a block diagram illustrating a portion of example implant device 700 shown in FIG. 7, consistent with embodiments of the present disclosure. In FIG. 8, sensor 740 of implant device 700 includes a first electrode connected to a first node 740A and a second electrode connected to a second node 740B.

In FIG. 8, microchip 730 may include a sensing circuit 810 for measuring one or more physiological parameter of an individual, and a sensor detector circuit 820 for detecting when sensor 740 interfaces with sensor interface 745 and/or when sensor 740 electrically couples with microchip 730. As shown in FIG. 8, first node 740A and second node 740B are connected to sensor detection circuit 820 and at least first node 740A is connected to sensing circuit 810. In some embodiments, second node 740B may also be connected to sensing circuit 810.

In some embodiments, sensing circuit 810 may be electrically connected to sensor detector circuit 820, for example, via an interconnect 830. Sensing circuit 810 and/or sensor detector circuit 820 may be electrically connected to and powered by battery 720. In some embodiments, microchip 730 may include a first chip including sensing circuit 810 and a second chip including sensor detector circuit 820.

In some embodiments, portions 812 of sensing circuit 810 may include an analog-to-digital converter (ADC) arranged to convert the current or voltage levels (or potential) at first node 740A to a digital signal. Additionally, or alternatively, portions 812 of sensing circuit 810 may include an amplifier (e.g., a transimpedance amplifier) for generating a voltage-based signal, or a current-based signal having a larger amplitude compared to the raw signal sensed at first node 740A. Furthermore, portions 812 of sensing circuit 810 may include a circuit that generates a voltage-or current-based signal having a different output impedance. Portion 812 of sensing circuit 810 may further include other circuit(s) for accurately measuring the current or voltage at first node 740A. In some embodiments, portions 812 of sensing circuit 810 may also connect to second node 740B. In these embodiments, portions 812 of sensing circuit 810 may further includes circuit(s) for accurately measuring the current or voltage at second node 740B.

In some embodiments, sensing circuit 810 may operate in one of at least two modes. In a first mode, sensing circuit 810 may be configured to consume zero or substantially zero power from a power source such as battery 720. In FIG. 8, for example, sensing circuit 810 includes one or more switches 814 between one or more portions 812 of sensing circuit 810 and battery 720. Switches 814 may be configured to create an open connection (i.e., preventing current from flowing) between portions 812 and battery 720 while sensing circuit 810 is in the first mode.

In a second mode, sensing circuit 810 may be configured to consume a sufficient power necessary to sense the current or voltage at first node 740A (and/or second node 740B). For example, in exemplary implant device 700 of FIG. 8, switches 814 may create a closed connection (i.e., allowing current to flow) between portion 812 and battery 720 while sensing circuit 810 is in the second mode. Therefore, the amount of power consumed by sensing circuit 810 in the second mode may be greater than the amount of power consumed by sensing circuit in the first mode.

In some embodiments, the operating mode of sensing circuit 810 may be determined based on an electrical signal from sensor detection circuit 820. For example, a first signal from sensor detection circuit 820 via interconnect 830 may cause sensing circuit 810 to operate in the first mode while a second signal from sensor detection circuit 820 via interconnect 830 may cause sensing circuit 810 to operate in the second mode. In this example, interconnect 830 may be coupled to switches 814 to control the supply of power from battery 820 to portions 812 of sensing circuit 810.

In some embodiments, while in the first mode and/or second mode, portions 812 of sensing circuit 810 may be configured to such that an input impedance is high (e.g., similar to an input impedance of an op-amp) so as to maximize the portion of current flowing to sensor detection circuit 820.

In some embodiments, sensor 740 may be configured to electrically couple the first and second electrodes. For example, sensor 740 may resistively, capacitive, and/or inductively couple the first and second electrodes of sensor 740. In these embodiments, when a signal is present at the second electrode of sensor 740, a corresponding signal that is based on the signal may be generated at the first electrode of sensor 740.

It will be appreciated that a circuit element may be a linear or a non-linear element, such as, but not limited to, a resistor, a capacitor, an inductor, a transistor, a memristor, a diode, a transistor, a switch, a current/voltage source, to provide some examples.

Figure 9:
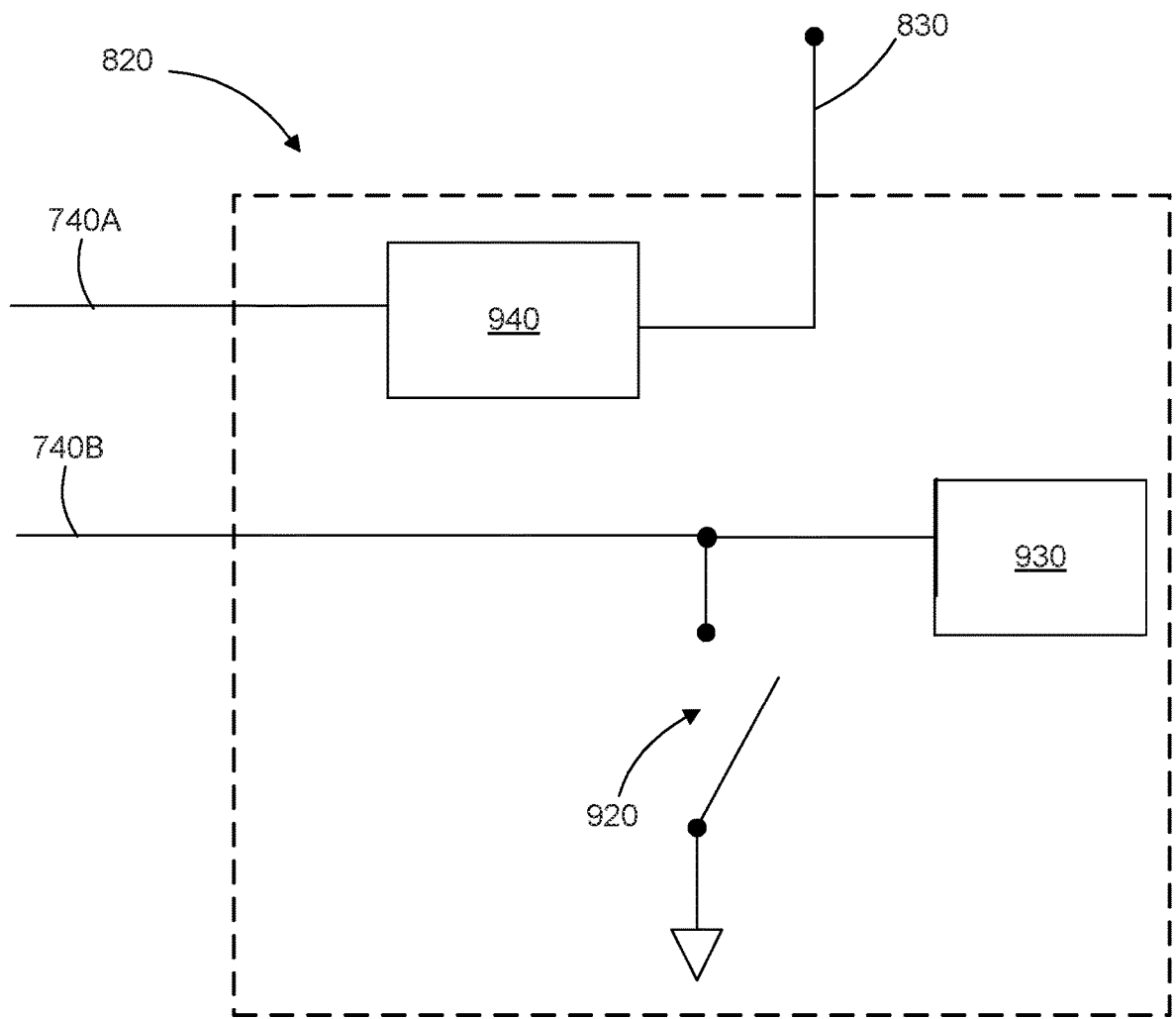
FIG. 9 is a circuit diagram of an example sensor detection circuit consistent with embodiments of the present disclosure.

FIG. 9 is a circuit diagram of an example sensor detection circuit 820 shown in FIG. 8, consistent with embodiments of the present disclosure. As disclosed herein, sensor detection circuit 820 may generate a first signal at interconnect 830 when sensor detection circuit 820 detects that sensor 740 is electrically decoupled from microchip 730 and a second signal at interconnect 830 when sensor detection circuit 820 detects that sensor 740 is electrically coupled with microchip 730. The generated signal, as noted above, may be used by sensing circuit 810 to determine the mode of operation. For example, the first signal generated by sensor detection circuit 820 may cause sensing circuit 810 to operate in a first mode while a second signal generated by sensor detection circuit 820 may cause sensing circuit 810 to operate in a second mode.

As shown in FIG. 9, sensor detection circuit 820 includes a signal generator 930 connected to second node 740B. In some embodiments, signal generator 930 may generate a voltage-based or a current based signal at second node 740B. In some embodiments, the signal generated by signal generator 930 may be an AC signal (voltage or current). Alternatively, the signal generated by signal generator 930 may be a DC voltage or DC current. In some embodiments, the signal generator may be a clock signal generator.

In some embodiments, as shown in FIG. 9, sensor detection circuit 820 may further include a switch 920 between second node 740B and ground. While sensing circuit 810 is in the first mode, switch 920 may be open such the voltage or current at second node 740B is the signal from signal generator 930. In some embodiments, however, while sensing circuit 810 is in the second mode, switch 920 may be closed such that second node 740 is electrically shorted to ground. That is, while sensing circuit 810 is in the second mode, second node 740B may be grounded even when signal generator 930 generates a signal. The grounding of second node 740B may increase the accuracy of sensing circuit 810.

As shown in FIG. 9, sensor detector circuit 820 may also include a signal detector 940 connected to first node 740A. Signal detector 940 may be configured to sense (or measure) voltage and/or current levels at first node 740A. Further, based on the sensed levels, signal detector 940 may generate the first or second signal at interconnect 830. This generated signal, as noted above, may be used by sensing circuit 810 to determine the mode of operation.

In some embodiments, the first signal and the second signal may be represented by one or more voltage or current levels. For example, the first signal may be represented by the supply voltage of microchip 730, while the second single may be represented by the ground-level voltage.

As discussed above, in some embodiments, sensor 740 may be configured to electrically couple the first and second electrodes. Further as discussed above, in these embodiments, when a signal is present at the second electrode of sensor 740, a corresponding signal that is based on the signal may be generated at the first electrode of sensor 740. In some embodiments, when sensor 740 interfaces with sensor interface 745, the first electrode of sensor 740 may electrically couple with first node 740A and the second electrode of sensor 740 may electrically couple with second node 740B. Therefore, when sensor 740 electrically couples to microchip 730, the signal generated by signal generator 930 at second node 740B may cause a corresponding signal to be generated at first node 740A (since sensor 740 may electrically couple first node 740A with second node 740B).

In some embodiments, sensor detector circuit 820 may determine that sensor 740 is electrically coupled to microchip 730 when the corresponding signal is detected at first node 740A. Further, sensor detector circuit 940 may determine that sensor 740 is electrically decoupled from microchip 730 when the corresponding signal is not detected at first node 740A. In some embodiments, the corresponding signal may be derived from the generated signal. Alternatively, or additionally, the corresponding signal may be substantially the same as the generated signal.

In one example, sensor 740 may be configured to capacitively couple the first and second electrodes of sensor 740. And, when sensor 740 interfaces with sensor interface 745, the first electrode of sensor 740 may electrically couple with first node 740A and the second electrode of sensor 740 may electrically couple with the second node 740B. Therefore, in this example, when signal generator 930 generates a first AC voltage signal having a first frequency at second node 740B, a second AC voltage signal may be generated at first node 740A since first node 740A and second node 740B are capacitively coupled via sensor 740. Further, the second AC voltage signal may have the same frequency as the first AC voltage signal.

Additionally, sensor detector circuit 940 may determine that sensor 740 is electrically decoupled with microchip 730 when an AC voltage signal having the same frequency is not detected at first node 740A, and determine that sensor 740 is electrically coupled with microchip 730 when an AC voltage signal having the same frequency is detected at first node 740A.

In some embodiments, sensor detector circuit 940 may include a threshold detector that generates an output signal based on the detected voltage or current at first node 740A. For example, the threshold detector of sensor detector circuit 940 may output a first signal at interconnect 830 when the voltage at first node 740A is below a threshold voltage or current and output a second signal once the voltage at first node 740A is above (or equal to) the threshold voltage.

In one example, sensor 740 may be configured to resistively couple the first electrode and the second electrode of sensor 740. Further, signal generator 930 may generate a first DC voltage-level (e.g., positive voltage) at second node 740B. When sensor 740 is electrically coupled to microchip 730, a second DC voltage level may be generated at first node 740A because first node 740A and second node 740B are resistively coupled via sensor 740. Further, the second DC voltage level may be lower than the first DC voltage level. In this example, the threshold detector of sensor detector circuit 940 may determine that sensor 740 is electrically decoupled from microchip 730 when a voltage level detected at first node 740A is below a threshold voltage, and determine that sensor 740 is electrically coupled to microchip 730 when a voltage level detected at first node 740A is above the threshold voltage.

In some embodiments, the threshold detector of sensor detector circuit 940 may determine that sensor 740 is electrically decoupled to microchip 730 when a voltage level detected at first node 740A is below a first threshold voltage, and determine that sensor 740 is electrically coupled to microchip 730 when a voltage level detected at first node 740A is above a second threshold voltage. In these embodiments, the first and second threshold voltages may be different.

Figure 10:
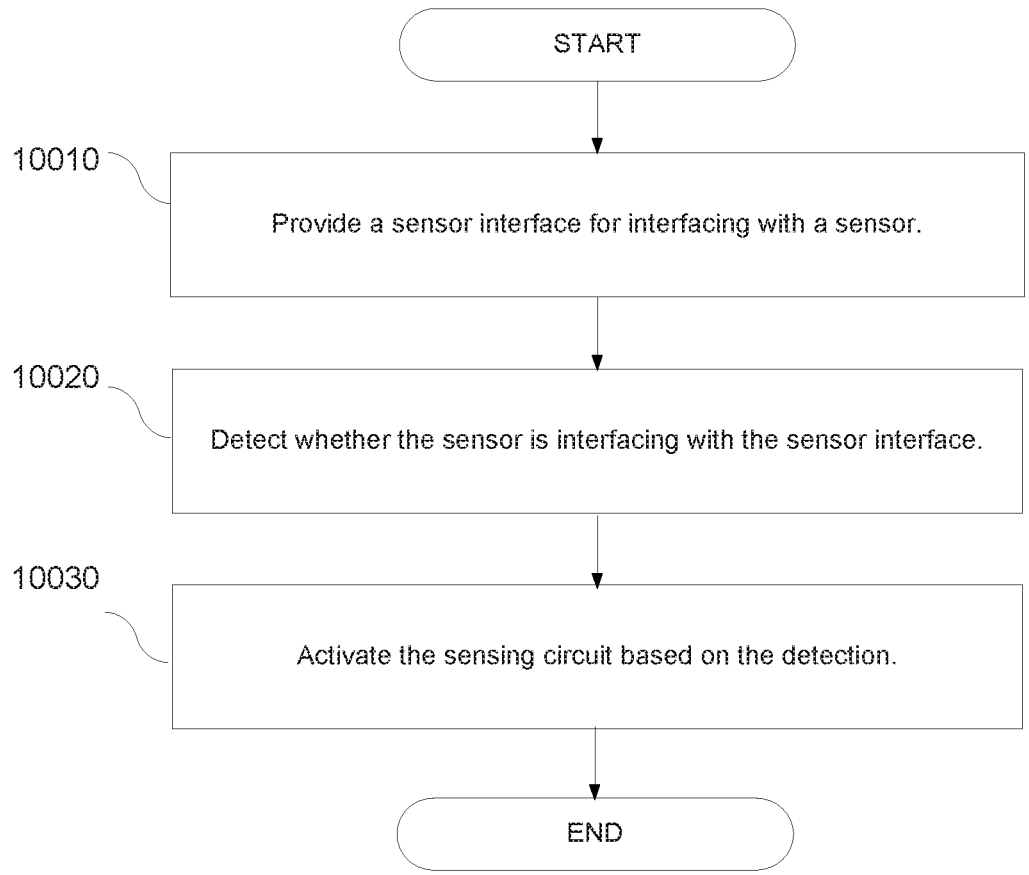
FIG. 10 is a flowchart of an example method consistent with embodiments of the present disclosure.

FIG. 10 is an illustrative process 10000 for activating a sensing circuit of an implant device for measure at least one physiological parameter of an individual using the sensor. At step 10010, a sensor interface for interfacing with a sensor is provided. At step 10020, a sensor detector may detect whether the sensor is interfacing with the sensor interface. At step 10030, the sensor detector may activate the sensing circuit based on the detection of whether the sensor interfacing with the sensor interface.

At an optional step, the sensor interface may interface the sensor. In some embodiments, the interfacing of the sensor interface with the sensor may include mechanically holding the sensor to the implant device. In some embodiments, the interfacing of the sensor interface with the sensor may include electrically coupling the sensor interface with the sensor. In some embodiments, the detection of whether the sensor is interfacing with the sensor interface may include sending a signal to the sensor interface and receiving a corresponding signal from the sensor interface when the sensor is interfacing with the sensor interface. In these embodiments, the corresponding signal is related to the signal. In some embodiments, the signal and the corresponding signal may have the same frequency. At an optional step, a sensing circuit, using the sensor, may measure the at least one physiological parameter of the individual after the interfacing of the sensor interface with the sensor. At an optional step, the sensor may de-interface the sensor interface re-interfacing the sensor interface.

In the preceding specification, various exemplary embodiments and features have been described with reference to the accompanying drawings. It will, however, be evident that various modifications and changes may be made thereto, and additional embodiments and features may be implemented, without departing from the broader scope of the invention as set forth in the claims that follow. For example, advantageous results still could be if components in the disclosed systems were combined in a different manner and/or replaced or supplemented by other components. Other implementations are also within the scope of the following exemplary claims. The specification and drawings are accordingly to be regarded in an illustrative rather than restrictive sense. Moreover, it is intended that the disclosed embodiments and examples be considered as exemplary only, with a true scope of the present disclosure being indicated by the following claims and their equivalents.

The invention claimed is:

1. An implant device comprising:
    a sensor interface configured to interface with a sensor;
    a sensing circuit that measures at least one physiological parameter of an individual; and
    a sensor detector configured to:
        detect whether the sensor is interfacing with the sensor interface; and
        activate the sensing circuit to permanently remain in a powered sensing mode based on the detection.

2. The implant device of claim 1, wherein the sensor interface includes a mechanical clamp for holding the sensor to the implant device.

3. The implant device of claim 1, wherein the sensor detector includes:
    a signal generator configured to send a signal to the sensor interface; and
    a signal detector configured to receive a corresponding signal from the sensor interface when the sensor is interfacing with the sensor interface, wherein the corresponding signal is related to the signal.

4. The implant device of claim 1, wherein the sensor includes a first sensor node and a second sensor node, and the sensor interface includes a first interface node and a second interface node, the sensor interface being further configured to electrically couple the first sensor node with the first interface node and the second sensor node with the second interface node.

5. The implant device of claim 4, wherein when the sensor is interfacing with the sensor interface, the sensor is configured to electrically couple the first and the second interface nodes.

6. The implant device of claim 4, wherein the sensor detector includes:

a signal generator configured to generate a signal at the first interface node of the sensor interface; and a signal detector configured to detect a corresponding signal at the second interface node of the sensor interface when the sensor is interfacing with the sensor interface, wherein the generated signal and the corresponding signal are related.

7. The implant device of claim 6, wherein the generated signal and the corresponding signal have the same signal frequency.

8. The implant device of claim 1, wherein at least one of the sensor detector and the sensing circuit is implemented in an integrated circuit.

9. The implant device of claim 1, wherein the sensor detector is implemented in a first integrated circuit and the sensing circuit is implemented in a second integrated circuit.

10. The implant device of claim 1, further comprising a power source that provides power to the sensing circuit and the sensor detector.

11. The implant device of claim 1, wherein the sensor interface is a re-matable interface.

12. A method for activating a sensing circuit of an implant device for measuring at least one physiological parameter of an individual, the method comprising:

providing a sensor and a sensor interface;

detecting whether the sensor is interfacing with the sensor interface; and activating the sensing circuit to permanently remain in a powered sensing mode based on the detection of whether the sensor is interfacing with the sensor interface.

13. The method of claim 12, further comprising:

interfacing the sensor interface with the sensor.

14. The method of claim 13, wherein the interfacing of the sensor interface with the sensor includes mechanically holding the sensor to the implant device.

15. The method of claim 13, wherein the interfacing of the sensor interface with the sensor includes electrically coupling the sensor interface with the sensor.

16. The method of claim 13, further comprising:

measuring the at least one physiological parameter of the individual using the sensor after the interfacing of the sensor interface with the sensor.

17. The method of claim 12, wherein the detection of whether the sensor is interfacing with the sensor interface includes:

sending a signal to the sensor interface; and receiving, in response to sending the signal, a corresponding signal from the sensor interface when the sensor is interfacing with the sensor interface.

18. The method of claim 17, wherein the signal and the corresponding signal have the same frequency.

* * * * *